United States Patent [19]

Niznick

[11] Patent Number: 5,076,788

[45] Date of Patent: Dec. 31, 1991

[54] GROOVED, CYLINDRICAL DENTAL IMPLANT ANCHORING MEANS

[75] Inventor: Gerald A. Niznick, Encino, Calif.

[73] Assignee: Core-Vent Corporation, Encino, Calif.

[21] Appl. No.: 253,685

[22] Filed: Oct. 5, 1988

[51] Int. Cl.$^5$ .............................................. A61C 8/00
[52] U.S. Cl. ................................... 433/173; 433/174
[58] Field of Search ............... 433/173, 174, 175, 176, 433/201.1, 220, 221

[56] References Cited

U.S. PATENT DOCUMENTS

| | | | |
|---|---|---|---|
| 2,857,670 | 10/1958 | Kiernan, Jr. ......................... | 433/175 |
| 4,239,489 | 12/1980 | Ellman et al. ........................ | 433/220 |
| 4,270,905 | 6/1981 | Mohammed .......................... | 433/173 |
| 4,468,200 | 8/1984 | Münch ................................. | 433/174 |
| 4,932,868 | 6/1990 | Linkow et al. ....................... | 433/174 |

FOREIGN PATENT DOCUMENTS

| | | | |
|---|---|---|---|
| 2600639 | 7/1976 | Fed. Rep. of Germany ...... | 433/174 |
| 2199502 | 7/1988 | United Kingdom ................. | 433/174 |
| 2199626 | 7/1988 | United Kingdom ................. | 433/174 |

Primary Examiner—Cary E. O'Connor

[57] ABSTRACT

A substantially cylindrically-shaped dental implant includes on its outer surface one or more longitudinally-extending grooves and, near the base of the implant, one or more transversely-extending openings that communicate with the grooves and with a chamber internal to the implant. The chamber also communicates through an upwardly-extending passage with an apical opening at the base of the implant to permit tissue, fluids and debris to escape from a jawbone opening formed to receive the implant.

11 Claims, 2 Drawing Sheets

GROOVED, CYLINDRICAL DENTAL IMPLANT ANCHORING MEANS

This invention relates to a cylindrical dental implant anchoring means having at least one, and preferably a plurality of longitudinally-extending grooves on its outer surface that communicate with at least one, and preferably a plurality of transverse openings at and near the base of the implant. The transverse openings communicate with an internal chamber near the bottom of the implant, and the chamber communicates with an apical opening at the bottom of the implant. The combination of these grooves, these openings and the chamber facilitate the outflow of fluids, tissue and other matter from openings in jawbone tissue formed to receive the implant.

The longitudinally-extending, slot-shaped grooves can vary in depth, length and width, but are preferably of equal depth, length and width on a single implant. These grooves provide means for receiving ingrowing bone tissue from the surface of an opening in bone tissue formed to receive the implant. Such ingrowing tissue minimizes rotation of the implant in the opening, and minimizes displacement of the implant from such an opening. In preferred embodiments, the grooves are spaced substantially equidistant from one another around the outer surface of the implant. Preferably there are two, three or four or more such grooves on a single implant. Preferably, these grooves extend substantially from the transverse openings to, or substantially to the top of the implant. The transverse openings in the exterior wall of the implant are preferably round, or substantially round in shape, and the number of such openings is preferably the same as the number of grooves.

At the bottom of the implant is an apical opening that leads to a longitudinally-extending opening that extends inwardly and upwardly to the internal chamber. The combination of grooves, transverse openings and internal chamber permit fluids, tissue and other substances that enter the implant through the apical opening, or through the transverse openings, or both, to pass upwardly through the slot-shaped grooves toward, or to, the top of the implant. These openings facilitate the flow of blood and other fluids, and tissue and other substances from a jawbone site formed to receive this dental implant.

In preferred embodiments, the exterior wall of the implant is substantially smooth except for the longitudinally-extending, slot-shaped grooves and the transverse openings. In alternative embodiments, the implant has, on its outer surface, at least one projection, at least one screw flight, or both, to facilitate anchoring the implant in a jawbone site.

The implant preferably has, at the top, means for attaching an insert to support a dental prosthesis. Preferably, this means includes an opening that extends downwardly and inwardly into the implant. This opening can be internally threaded for engagement with a threaded post on a dental implant insert; smooth-walled; or partially smooth-walled and partially internally threaded. In preferred embodiments, the internal opening also includes, near the top of the implant, an internal wrench-engaging portion for receiving a tool such as an Allen wrench or other tool to assist in placing the implant in a jawbone site. In preferred embodiments, the inner surface of the opening at the top of the implant is chamfered to engage a complementary-shaped insert and to provide support, especially lateral support, against forces impinging on prostheses attached to the insert.

This invention will be further described with reference to an illustrative embodiment in connection with the attached drawings in which.

Figure 1:
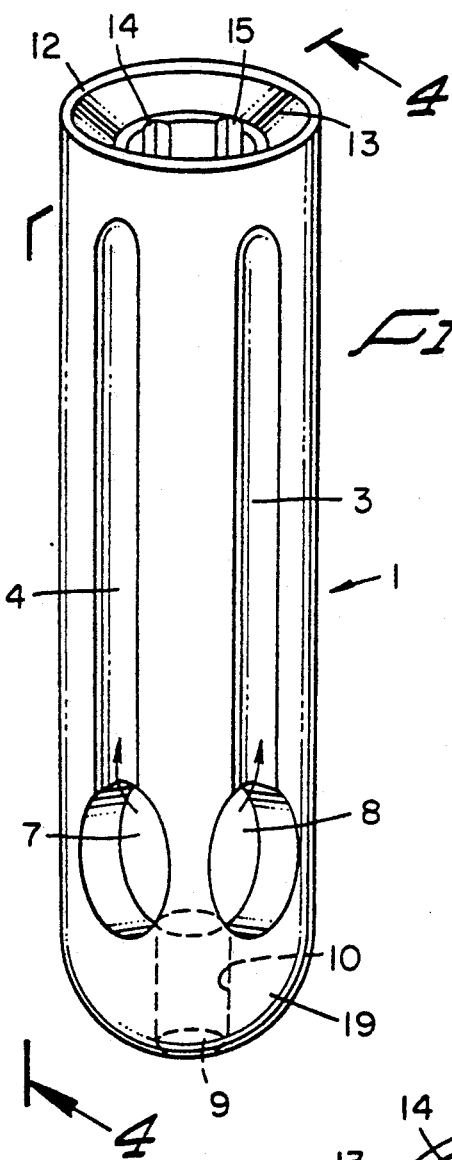
FIG. 1 is a perspective view of a preferred embodiment of the dental implant anchoring means of this invention.
Figure 2:
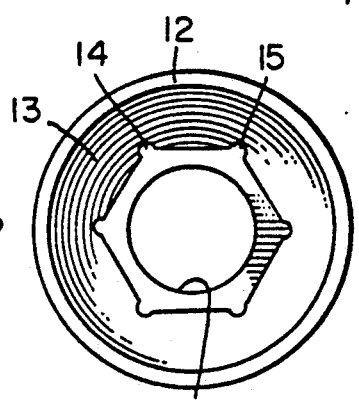
FIG. 2 is a top plan view of the implant anchoring means shown in FIG. 1.
Figure 3:
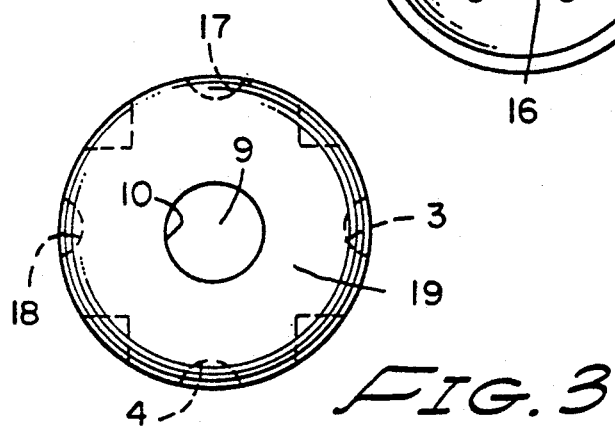
FIG. 3 is a bottom plan view of the implant anchoring means shown in FIGS. 1 and 2.
Figure 4:
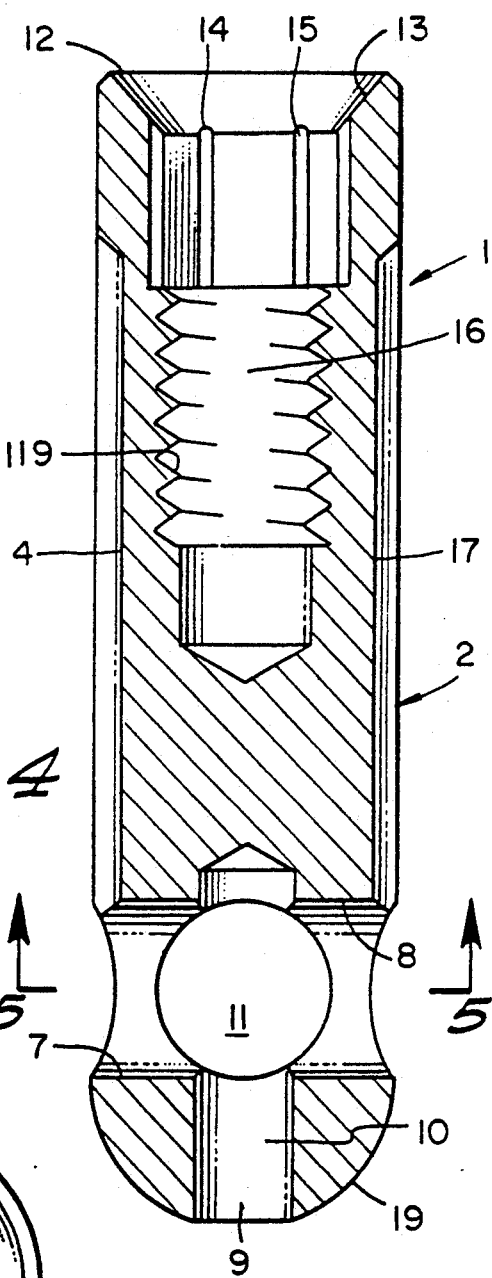
FIG. 4 is a cross-sectional view, taken on line 4—4 of FIG. 1, of the implant anchoring means shown in FIGS. 1-3.
Figure 5:
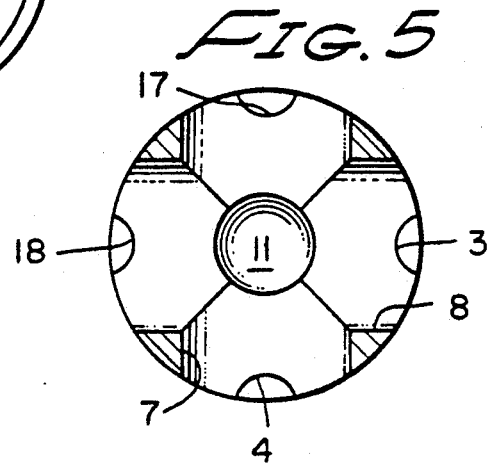
FIG. 5 is a cross-section view, taken on line 5—5 of FIG. 4, of the implant anchoring means shown in FIGS. 1-4.

Referring now to the drawing, cylindrically-shaped implant 1, preferably made from a metal such as unalloyed titanium or the titanium/6-aluminum/4-vanadium Eli alloy, has an outer surface 2, that includes a plurality of longitudinally-extending grooves 3, 4, 17 and 18, spaced substantially equidistant from one another around surface 2. The bottom end of each of these grooves 3, 4, 17 and 18 communicates with a round-shaped opening such as openings 7 and 8. Openings 7 and 8 lead into interior chamber 11 near the bottom surface 19 of implant 1. Bottom surface 19 of implant 1 includes apical opening 9 which leads into upwardly extending, cylindrically-shaped passage 10 that, in turn, communicates with interior chamber 11.

When implant 1 is seated in a cylindrically-shaped opening in jawbone tissue, fluid, tissue and other debris at the bottom of the jawbone opening enter chamber 11 through apical opening 9 and passage 10. These substances accumulate in, then exit chamber 11 through openings 7 and 8 that communicate with longitudinally-extending grooves 3 and 4. These openings and grooves permit the tissue, blood, other fluids and other debris to pass upwardly through grooves 3, 4, 17 and 18 to or toward the top of the edge 12 of implant 1, and then out of the jawbone opening formed to receive implant 1.

Implant 1 also includes, at top edge 12, a downwardly-extending inner opening 16 having a chamfered surface 13 at or near the top edge 12 that extends downwardly and inwardly toward inner opening 16. Near the top of inner opening 16 is a hex-shaped region 14, 15 formed to receive a hex-shaped tool such as an Allen wrench. Below surface 14, 15 is internally threaded shaft 119. This shaft is formed to engage threads on the post of a dental insert (not shown). The post has an externally-threaded surface for engaging the internal threads in passage 16 and for securing the post and prosthesis joined thereto in inner opening 16.

Figure 6:
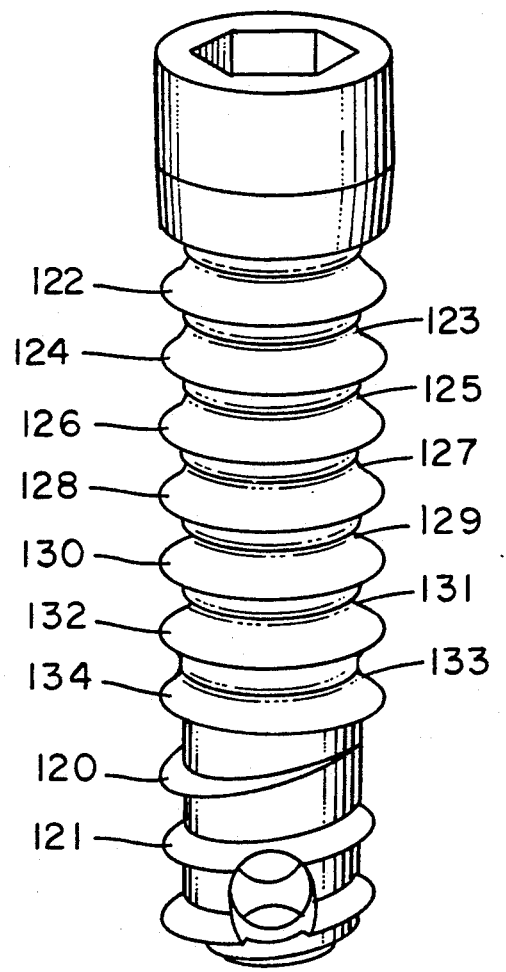
FIG. 6 shows an elevation view of a dental implant having both projections and screw flights on its exterior surface.

FIG. 6 shows a dental implant that includes both screw flights 120, 121 and projections 122-134 on its exterior surface.

What is claimed is:

1. Dental implant anchoring means having a base and a substantially right circular cylindrically-shaped outer surface, said outer surface including substantially no thread means thereon, and including, on said outer surface, at least one longitudinally-extending, slot-shaped groove; near the base of said implant, at least one transversely-extending opening; inside and near the base of said anchoring means, an internal chamber communicating with said at least one transversely-extending opening; and, at the base of said implant, an apical opening communicating through an upwardly-extending passage with said internal chamber, wherein said at least one groove communicates with at least one transversely-extending opening.

2. The dental implant anchoring means of claim 1 further comprising a plurality of said grooves and a plurality of said transverse openings.

3. The dental implant anchoring means of claim 1 wherein each of said grooves communicates directly with one, and only one, of said transverse openings.

4. The dental implant anchoring means of claim 1 further comprising an opening at the top of said implant, said opening having a size and shape adapted to receive a dental insert that fits within said opening at the top of said dental implant.

5. The dental implant of claim 4 further comprising within said opening at the top of said implant, a downwardly-extending passage, said passage having thread means on at least a portion of its surface.

6. Dental implant anchoring means having a base and a substantially right circular cylindrically-shaped outer surface, said outer surface including substantially no thread means thereon, and including, on said outer surface, at least one longitudinally-extending, slot-shaped groove; near the base of said implant, at least one transversely-extending opening; and inside and near the base of said anchoring means, an internal chamber communicating with said at least one transversely-extending opening, wherein said at least one groove communicates with said at least one transversely-extending opening.

7. The dental implant anchoring means of claim 6 further comprising a plurality of said grooves and a plurality of said transverse openings.

8. The dental implant anchoring means of claim 7 wherein each of said grooves communicates directly with one, and only one, of said transverse openings.

9. The dental implant anchoring means of claim 6 wherein said outer surface includes at least one projection.

10. The dental implant anchoring means of claim 6 further comprising an opening at the top of said implant, having a size and shape adapted to receive a dental insert and including a post means that fits within said opening at the top of said dental implant.

11. The dental implant of claim 10 further comprising, within said opening at the top of said implant, a downwardly-extending passage, said passage having thread means on at least a portion of its surface.

* * * * *